US011607184B2

(12) United States Patent
Hui et al.

(10) Patent No.: US 11,607,184 B2
(45) Date of Patent: Mar. 21, 2023

(54) MULTI-MODAL IMAGE-GUIDED RADIATION SYSTEM

(71) Applicants: City of Hope, Duarte, CA (US); The Regents of the University of California, Oakland, CA (US)

(72) Inventors: Susanta K. Hui, Duarte, CA (US); Gultekin Gulsen, Duarte, CA (US); Farouk Nouizi, Irvine, CA (US)

(73) Assignees: City of Hope, Duarte, CA (US); The Regents of the University of California, Oakland, CA (US)

( * ) Notice: Subject to any disclaimer, the term of this patent is extended or adjusted under 35 U.S.C. 154(b) by 213 days.

(21) Appl. No.: 16/885,903

(22) Filed: May 28, 2020

(65) Prior Publication Data

US 2020/0375558 A1 Dec. 3, 2020

Related U.S. Application Data

(60) Provisional application No. 62/855,148, filed on May 31, 2019.

(51) Int. Cl.
| | | |
|---|---|---|
| *A61B 6/00* | (2006.01) | |
| *A61B 6/03* | (2006.01) | |
| *A61B 5/00* | (2006.01) | |
| *A61N 5/10* | (2006.01) | |

(52) U.S. Cl.
CPC .......... *A61B 6/4417* (2013.01); *A61B 5/0035* (2013.01); *A61B 5/0071* (2013.01); *A61B 5/0073* (2013.01); *A61B 6/035* (2013.01); *A61B 6/037* (2013.01); *A61B 6/5247* (2013.01); *A61N 5/1081* (2013.01); *A61B 6/4085* (2013.01); *A61B 6/508* (2013.01); *A61N 5/1049* (2013.01); *A61N 2005/1052* (2013.01); *A61N 2005/1061* (2013.01)

(58) Field of Classification Search
CPC ..... G01T 1/2985; A61B 6/4417; A61B 6/037; A61B 6/5247; A61B 5/0035; A61B 5/0071
See application file for complete search history.

(56) References Cited

U.S. PATENT DOCUMENTS

| | | | | |
|---|---|---|---|---|
| 2012/0253174 | A1* | 10/2012 | Popescu | A61B 6/42 600/411 |
| 2012/0265050 | A1* | 10/2012 | Wang | A61B 6/485 600/407 |
| 2016/0209514 | A1* | 7/2016 | Moskal | A61B 6/037 |
| 2020/0345322 | A1* | 11/2020 | Bai | A61B 6/4266 |

* cited by examiner

*Primary Examiner* — Carolyn A Pehlke
(74) *Attorney, Agent, or Firm* — Mintz Levin Cohn Ferris Glovsky and Popeo, P.C.

(57) ABSTRACT

Systems and methods relate to multi-modal imaging of tissue combined with highly focused radiation interventions. The system is a portable multimodal imaging unit that integrates imaging and image analysis. The system can be retrofitted to use with any commercial radiation therapy machine. In one aspect, a system integrates various imaging modalities into a single, coordinated structure. The system integrates X-ray and cone beam computed tomography (CBCT), optical imaging (such as bioluminescent imaging (BLI), fluorescence tomography (FT)), and positron emission tomography (PET) imaging in a single, self-contained structure.

15 Claims, 3 Drawing Sheets

MULTI-MODAL IMAGE-GUIDED RADIATION SYSTEM

CROSS-REFERENCE TO RELATED APPLICATION

This application claims the benefit of U.S. Provisional Patent Application No. 62/855,148 filed May 31, 2019, the contents of which is incorporated herein by reference in its entirety and for all purposes.

BACKGROUND

Humans and/or small animals with tumors can be irradiated such as for research or treatment purposes. Prior to such irradiation, a relatively exact location of tumor must be identified. This enables proper guidance of the treatment X-Rays to the tumor.

Existing irradiation systems for small animals use single-mode computed tomography (CT) imaging. However, CT, provides 3D anatomical/geometric information, cannot easily distinguish well between normal and tumorous tissue given that a tumor is biologically and physiologically different but not anatomically different relative to healthy tissue. It would be beneficial to provide other imaging modalities in connection with irradiation systems for small animals.

In addition, the tumor vasculature is a critical component of the tumor microenvironment (TME). This vasculature is essential for tumor growth and metastasis. An increasing number of cancer patients are treated with high dose of radiation using radiation therapy such as stereotactic body radiation therapy (SBRT) or stereotactic radiation surgery (SRS), both of which have been highly effective. However, the biological principle underlying the hypo-fractionated radiotherapy is unclear. Emerging evidence suggest that the SBRT and SRS affect tumor vascular microenvironment. Apart from direct radiation induced cell killing, large cell death may be a result of indirect effect of vascular damage. As the tumor grows larger, the tumor vascular system also becomes spatially heterogeneous. Although static histological evaluation provided basis for rationalizing requirement of vascular assessment, it limits longitudinal studies in same subjects and complicates the investigation of the entire tumor region to monitor response of SBRT in real-time.

In view of the foregoing, non-invasive or minimally invasive, low-cost imaging techniques that allow dynamic measurements of vascular physiological functions in real-time are needed.

SUMMARY

Disclosed are systems and methods related to multi-modal imaging of tissue combined with highly focused radiation intervention(s). The system is a portable multimodal imaging unit that integrates imaging and image analysis. In an example implementation, the system can be retrofitted to use with any commercial radiation therapy machine. In one aspect, a system integrates various imaging modalities into a single, coordinated structure. In an example embodiment, the system integrates X-ray and cone beam computed tomography (CBCT), optical imaging (such as bioluminescent imaging (BLI), fluorescence tomography (FT)), and positron emission tomography (PET) imaging in a single, self-contained structure.

The disclosed systems and methods enable non-invasive monitoring of tumor vascular response to low-dose to high-dose irradiation, which can be a key to understanding TME. The system disclosed herein is a compact hybrid theranostic system that, in a non-limiting example, incorporates a Fluorescence Molecular Imager into a commercial microCT-guided irradiator. The system overcomes the limitations of single imaging modality systems as it allows the delivery of high-dose radiations. It also longitudinally monitors the tumor vascular response by quantifying the variation in the pharmacokinetics of an intravascular-injected fluorescent agent. The system is configured to guide radiation delivery to a location of a tumor based on tumor biological function and TME. The system can perform longitudinal imaging in regard to rapid response assessment. That is, the system enables rapid response assessment—such as within minutes—of treatment delivery based on the integrated modalities of the system. The integrated system also allows changing the mode of treatment delivery depending on immediate treatment response.

The system overcomes the limitations of single imaging modality systems by allowing high-dose radiation followed by longitudinal monitoring of tumor vascular response (TVR) by quantifying variation in the pharmacokinetics of an intravenously-injected fluorophore. In an exemplary method, a high dose radiation is applied to a target followed by longitudinal monitoring of TVR using the disclosed system.

A dedicated pixel-by-pixel data analysis method can be implemented and employed to perform the quantification for the TME changes. High-dose radiation causes a considerable TME variation that can be observed as a temporal delay in the kinetics of the fluophore as a result of vascular leakage. The disclosed systems and methods enable obtaining of valuable information by spatially describing the heterogeneous vascular response across the tumor and rapid response.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
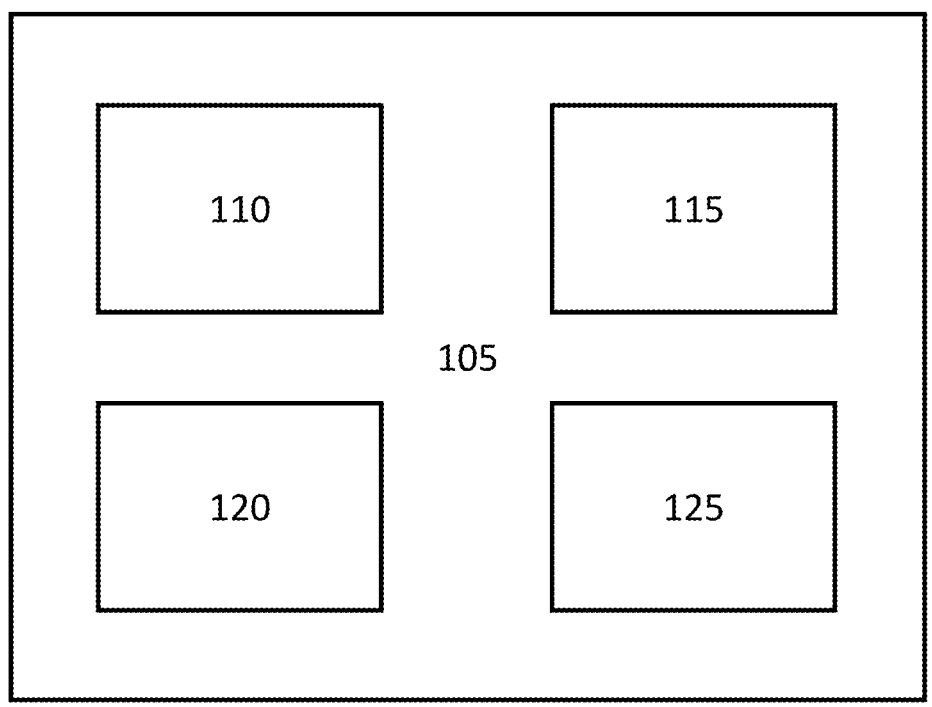
FIG. 1 is a schematic representation of a multi-modal imaging system.

Disclosed are systems and methods for multi-modal imaging combined with highly focused radiation intervention(s). In one aspect, a system integrates multi-modal imaging within a small animal (or human-sized) irradiator to optimize treatment and ultimately translate a robust means of controlling radiation therapy to patients.

Molecular imaging has tremendous potential to improve the use of external beam radiation therapy for the treatment of cancer and other disease. Such imaging can be configured to better identify cancer specific targets, and enhance the design of targeted radiation delivery to the target, monitor response to treatment, and minimize collateral damage to normal tissue. The use of such imaging to support more precise radiation targeting to the biological target volume (BTV) is increasingly becoming a focus of radiation research as it allows for further dose escalation to BTV tumor subregions. Single platform systems are disclosed herein that are capable of both molecular diagnostic and targeted external beam radiation therapy treatment techniques. The system includes a PET imaging component integrated with a cone beam computed tomography (CBCT) and those calculated targeted radiation treatment component.

The disclosed systems provide several advantageous features including, for example, noninvasive and real-time visualization of tumors, measurement of physiological or pathological processes in living systems and at the cellular and molecular levels, and an effective method of detecting 3D disease distribution in the TME. The disclosed systems and methods also are configured to deliver radiation in functional space and to evaluate initial treatment efficacy and associated biological function. Using the disclosed systems and methods, an end user can quantify "molecular efficacy" in vivo in real time at the start of therapy to identify likely responders and non-responders and thereby enable further treatment optimization by augmenting dose painting (i.e., applying a non-uniform dose of radiation to a tumor), leading to personalized precision medicine.

The disclosed system is configured to identify the specific BTV by visualizing delivery of tumor-specific anti-cancer agents, enabling precise delivery of radiation to the BTV as compared to conventional radiation targeting of the ATV. This can be difficult to assess for deep-seeded tumors as the lack of difference in tissue density prevents distinguishing tumor from neighboring normal tissues. An onboard imaging system enables real-time monitoring of rapid radiation response. This further enables rapid changing of treatment strategies and initiation of biological adaptive radiation therapy.

By combining several existing modalities, the system provides a comprehensive physiological and physical view of tumors in both the spatial and temporal dimensions and overcomes the limitations of the individual modalities. For example, PET imaging provides noninvasive, quantitative assessment of radiotracer uptake through deep tissue and whole-body assessment of distribution. In contrast, fluorescence probes are stable and may complement PET in terms of serial imaging, improved temporal resolution, availability, cost, ease of use, and use of non-ionizing radiation for longitudinal studies.

FIG. 1 is a schematic representation of a multi-modal imaging system 105. The system 105 can includes various components for imaging and/or irradiating tissue integrated into a single structure, which may be a monolithic structure. For example, the system 105 can include a Positron Emission Tomography (PET) component 110, a bioluminescent imaging (BLI) component 115, a fluorescence tomography component 120, and a cone-beam computed tomography with a highly focused radiation intervention component 125 for use in preclinical cancer models. The components 110, 115, 120, and 125 are all physically attached to a single housing or structure that enables the components to be used in conjunction with one another such as pursuant to a single, unified procedure. For example, the components can be removably or fixedly attached to a single platform such as a table top. In addition, one or more of the components can be fixedly and/or movably mounted on the structure relative to any of the other components such that one component can linearly and/or rotatably move relative one of the other components in a controlled and/or measurable manner. In an example embodiment, one or more of the components cannot be removed from the structure without damaging one or more of the components and/or the structure.

In a non-limiting example, the PET component 110 includes or incorporates two rotating PET components, such as a Hamamatsu TOF-PET modules EVA.KIT1-DEMO. Each module can be, for example, a 12×12 array of Lutetium Fine Silicate (LFS) scintillating crystals wherein each crystal is 4.14×1.14×20 mm3 with a pitch of 4.2 mm forming a total active area of 53.1×53.1 mm2. The component employs a scintillator signal that is read by a 12×12 array of 4×4 mm2 Multi-Pixel Photon Counter (MPPC) photodetectors using 1-to-1 coupling.

In another example embodiment, the PET component includes an array of PET devices arranged in a predetermined spatial arrangement, such as in a hexagonal array. For example, the PET component can include six detector modules that surround tissue to be monitored, such as a mouse for example. Such a spatial arrangement can provide, for example, a 50 mm axial field of view. A PET system in such an arrangement can acquire data and reconstruct images without requiring any rotation, which can provide for a faster imaging process. The configuration may include, for example, a 28×28 array of 1.76×1.76×10 mm3 LFS crystal elements coupled to a 16×16 array of 3×3 mm2 silicon photomultipliers. The total detector active area is 48×48 mm in a 50 mm wide package. The PET modules can be tiled with little dead space between them to form annular detector arrays around the subject for solid angle coverage and sampling. The PET modules are connected to a series of electronic boards that can provide power, collect single events, and determine coincidence events. In an embodiment, the PET modules generate images with the spatial resolution of approximately 2.6 mm is just an example.

In another example embodiment, the PET component comprises two rotating Hamamatsu time-of-flight PET modules positioned with a bore diameter of 101.6 mm and a radial field-of-view of 53.1 mm.

The PET component 110 can be placed on or otherwise coupled to a rail holder 14 (FIG. 2), which allows a user to change a distance or otherwise vary a spatial relationship between two or more PET components 110 coupled to the rail holder 14. The rail holder 14 can be configured to rotate together with another component around an iso-center of the system. The transaxial FOV (i.e., a distance between the PET modules) can be, for example, 101.6 mm. The PET component can be configured to slide away from a rotational plane such as to bring other components closer and to reduce radiation exposure. Acquisition software can be coupled to the system to record single events and data such as energy of a detected gamma, its time stamp and a crystal ID. The data can be recorded in rising order of the time stamp. The single events are then post-processed by a locally coincidence-sorting software to form a list of coincidences for further image reconstruction.

The optical imaging component can perform both FT and BLI. In a nonlimiting example, an ICCD camera equipped with an 18 mm GEN III GaAs image intensifier tube (Stanford Photonics) is used for both imaging modes. The disclosed system is configured to detect heterogeneity in tumor biology by PET imaging of Carcinoembryonic antigen (CEA) expressions. In addition, PET imaging can be used to simulate dose escalation to a sub volume of the anatomical tumor boundary while minimally increasing dose to the surrounding normal tissue. This enables PET guided heterogeneous dose increases to tumor subvolumes.

Figure 2:
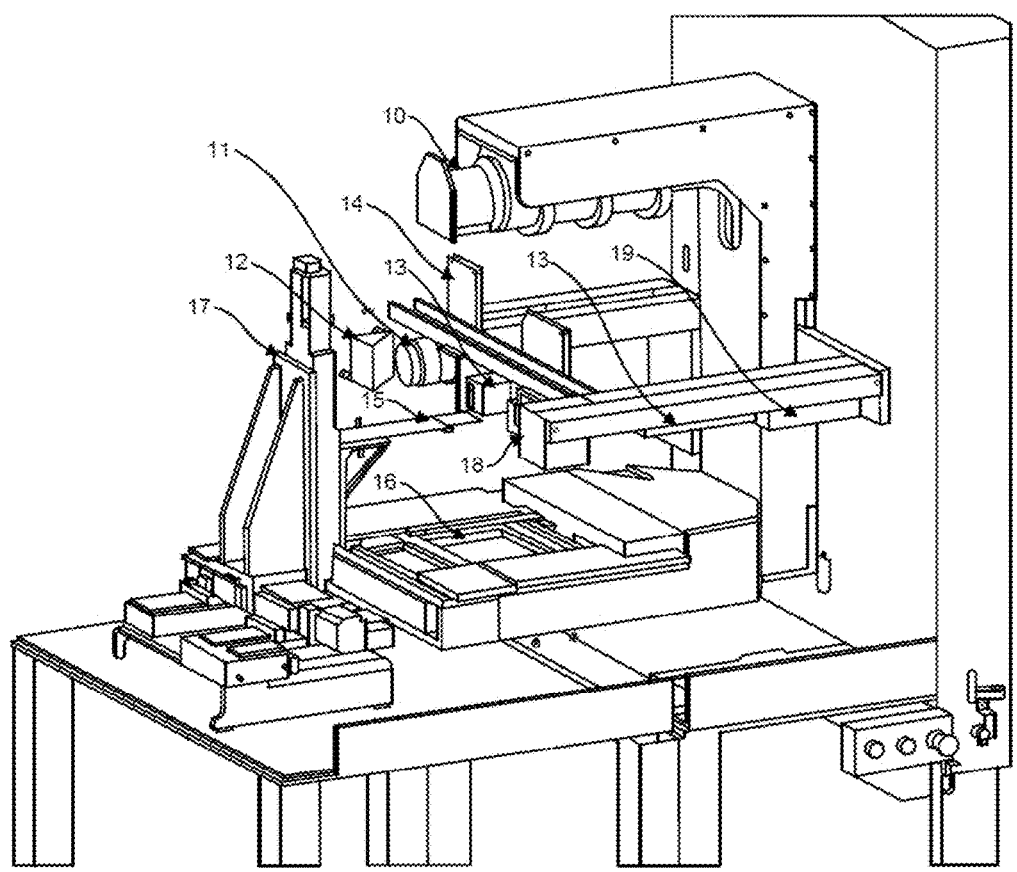
FIG. 2 shows an example of a Multi-modal image-guided radiation intervention system.

FIG. 2 shows a non-limiting example embodiment of a theranostic instrument, sometimes referred to as a multi-modal-imaging, radiation response and operation research system (sometimes referred to as MIRRORS.) As mentioned, the system combines (1) Positron Emission Tomography (PET), (2) bioluminescent imaging (BLI), (3) fluorescence tomography, and (4) cone-beam computed tomography with a highly focused radiation intervention for use in preclinical cancer models. The system provides comprehensive, noninvasive measures of tumors and the tumor microenvironment (TME) before, during, and post-intervention, to improve tumor targeting and treatment management.

With reference to FIG. 2, the system is fixedly mounted on a support structure, such as a flat-top table (although other structures can be used). An X-ray source 10 is mounted on a support arm, as is a camera 11. The support arm enables the x-ray source 10 and camera to be positioned in a fixed and defined relationship relative to the support structure. A reflective element, such as a mirror 12 (e.g., a 45-degree mirror), is also mounted on the support structure and configured to obtain an image. A PET detector 13 and PET electronic component are also both coupled to the support structure such as in a fixed or movable manner. The system further includes an X-ray camera 16, a scanner 18, as well as scanner electronics 19 for operating the scanner, and a laser emitter 20. The system is configured to image and otherwise interact with a specimen that can be positioned on a specimen holder 15, which can be movably positioned by a specimen positioning system 17 relative to two or three degrees of freedom.

It should be appreciated that the size of the support structure can vary. In addition, the specimen holder 15 can be sized and shaped to receive and support tissue specimens of various sizes.

The system is configured to integrate optical and PET detection systems with cone beam computed tomography (CBCT) on a high precision C-arm that can be moved in a controlled manner. The rotating arm can be configured to have a center of rotation for new imaging system with radiation delivery system. This maintains high precision accuracy between imaging center and center of radiation delivery and also enables the system to be portable so as to be used in other systems. It should be appreciated that some components of the system can be mounted on a separate structure although keeping the components mounted on a common, single structure and to the arm allow synchronization of center rotation and degree rotation.

The c-arm can be a component of a rotating commercial X-ray system with a high precision X, Y, Z stage at the isocenter of the system. The system can further reconstruct images (phantoms and ex vivo) from hybrid anatomical and functional imaging using an algorithm and can also perform automated co-registration of multi-modal images using an advanced software platform integrated with the system.

In addition, the system can measure target volumes accurately, asses the TME, and deliver effective radiation targeting BTV as compared to conventional radiation, where radiation is targeted to anatomy. Using two tumor models, the system measures ATV, BTV, and % difference of tumor volume and radiation dose coverage to evaluate radiation targeting efficacy. In addition, the system also measures tumor vascular dynamics (perfusion and permeability) and hypoxia (hypoxic volume and $SUV_{max}$) using indocyanine green (ICG) kinetics and FMISO PET. Measurement of precise BTV and TME changes enhances the efficacy of radiation delivery efficacy.

The system is further configured to measure post-treatment BTV as compared to ATV, and tumor vascular dynamics during and after treatment. Biological response (BTV) to treatment may be faster than changes in tumor size (anatomical tumor volume or ATV, measured by CT scan). The system thus assists in early responders and non-responders to develop personalized treatment for individuals. Often a post treatment tumor appears to progress by size or ATV. It is also known as "pseudo progression" of disease. This may be because of swelling or other radiation effect, without actually increasing the BTV. Thus, having the option of measuring BTV, can evaluate actual treatment response. This is important, as one would otherwise (based on ATV) stop treatment based on assuming the treatment is not effective.

Figure 3:
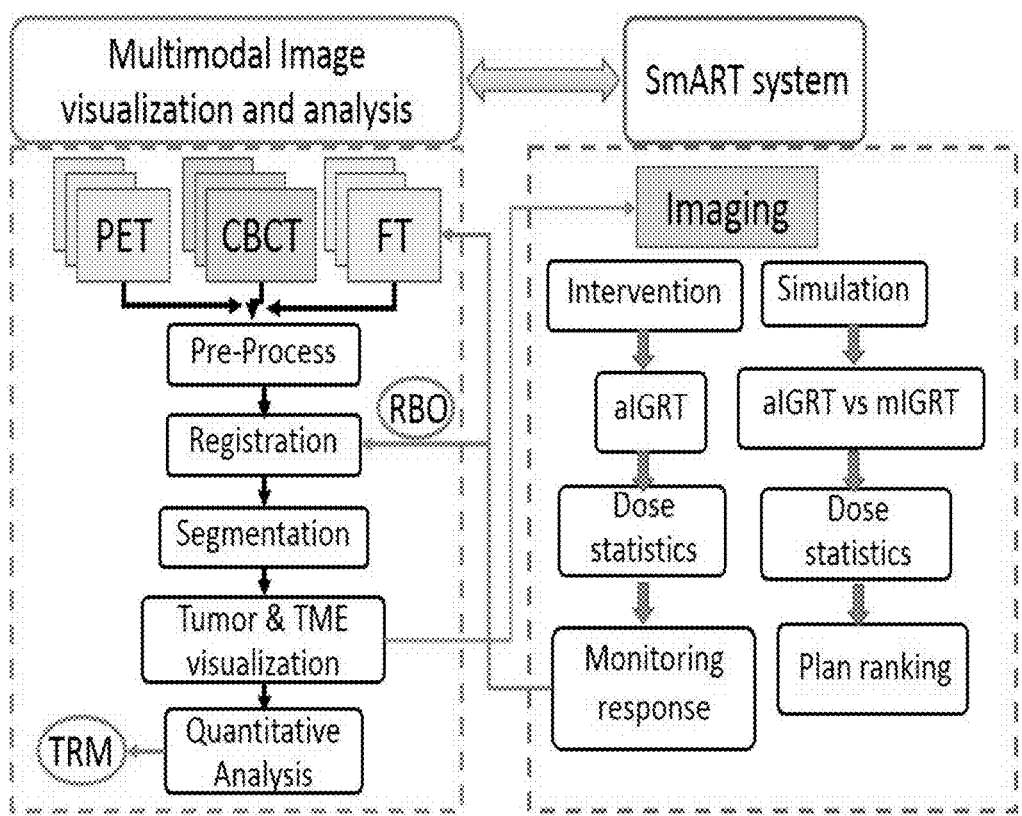
FIG. 3 shows an exemplary software layout that is configured to trigger the imaging and storage of the imaging results into and appropriate software database file structure for co-registration of the new imaging modalities with the existing cone-beam CT.

Software controls are configured for use with the imaging modalities. FIG. 3 shows an exemplary software layout that is configured to trigger the imaging and storage of the imaging results into and appropriate software database file structure for co-registration of the new imaging modalities with the existing cone-beam CT. An image analysis module provides integrated data analysis features for image preprocessing and registration using an atlas-based segmentation method.

The image processing software package represented in FIG. 3 is installed in the system, wherein the software enables offers multi-modal imaging registration (rigid and deformable registration), visualization module, and analysis modules. In an embodiment, the image analysis module provides integrated data analysis features for image preprocessing and registration using an atlas-based segmentation method. The performance of multi-modal image registration can be important for an image analysis workflow, and image registration algorithms depend on the magnitude of the deformation.

With reference still to FIG. 3, the software further includes an analytical module, "Response Based Optimizer" (RBO), to optimize the configuration of the registration algorithm based on the treatment response captured with imaging following treatment. Understanding the range of geometric variation among the modalities assists in optimizing registration algorithm selection and configuration for each follow-up imaging cycle for tissue being analyzed. The RBO further provides useful information for tracking the inter-modality variation during treatment, which optimizes the quantitative analysis (such as tumor volume) based on this dynamic setting. Such data is used as input for a mathematical model "tumor response modeling" (TRM) to monitor tumor growth and its response to RT, considering tumor volume and vascular changes.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random-access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, Wi-Fi (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore, the spirit and scope of the appended claims should not be limited to the description of the embodiments contained herein.

The invention claimed is:

1. A system for multi-modal imaging of tissue, comprising:
   a support structure;
   a Positron Emission Tomography (PET) component mounted on a straight rail coupled to the support structure, wherein the rail is interposed between an x-ray source suspended on a support arm and an x-ray camera below the support arm;
   a bioluminescent imaging (BLI) component mounted on the support structure;
   a fluorescence tomography component mounted on the support structure; and
   a cone-beam computed tomography component mounted on the support structure;
   wherein all the components are physically attached to the support structure that enables the components to be used in conjunction with one another pursuant to a single, unified procedure.

2. The system of claim 1, wherein at least a first component is fixedly or movably mounted on the support structure relative to at least one other of the components such that first component can linearly or rotatably move relative one of the other components in a controlled or measurable manner.

3. The system of claim 1, wherein the PET component includes two PET components.

4. The system of claim 3, wherein each of the two PET components rotate relative to the support structure.

5. The system of claim 4, wherein each of the two PET components are coupled to the rail.

6. The system of claim 5, wherein the rail permits a change in a spatial relationship between the two PET components.

7. The system of claim 5, wherein the rail can rotate together with another component around an iso-center of the system.

8. The system of claim 1, wherein the support structure is a table.

9. The system of claim 1, wherein the system is configured to reconstruct images from hybrid anatomical and functional imaging.

10. The system of claim 1, wherein the PET component can slide relative to at least one of the BLI component, the fluorescence tomography component, and the cone-beam computed tomography on the support structure.

11. A method of imaging tissue, comprising:
providing an imaging system comprising:
- a support structure;
- a Positron Emission Tomography (PET) component mounted on a straight rail coupled to the support structure, wherein the rail is interposed between an x-ray source suspended on a support arm and an x-ray camera below the support arm;
- a bioluminescent imaging (BLI) component mounted on a straight rail coupled to the support structure;
- a fluorescence tomography component mounted on the support structure; and
- a cone-beam computed tomography component mounted on the support structure;
- wherein all the components are physically attached to the support structure that enables the components to be used in conjunction with one another pursuant to a single, unified procedure; and performing an imaging procedure on the tissue.

12. A method as in claim 11, wherein the imaging system includes two PET components.

13. A method as in claim 12, further comprising rotating the two PET components relative to one another while the PET components remain physically attached to the support structure.

14. A method as in claim 12, further comprising moving at least one of the PET components along the rail.

15. A method as in claim 11, further comprising rotating the rail about an iso-center of the imaging system.

* * * * *